United States Patent [19]

Blouin

[11] Patent Number: 4,734,401

[45] Date of Patent: Mar. 29, 1988

[54] PROCESS FOR SPRAY DRYING AMINO ACID COMPOSITIONS

[75] Inventor: John J. Blouin, Catonsville, Md.

[73] Assignee: W. R. Grace & Co., New York, N.Y.

[21] Appl. No.: 840,307

[22] Filed: Mar. 17, 1986

[51] Int. Cl.$^4$ .................... A23B 4/04; A61K 9/10; A61K 37/02

[52] U.S. Cl. .......................... 514/14; 514/2; 426/443; 426/471; 426/478

[58] Field of Search .............. 426/443, 471, 478; 514/2, 14

[56] References Cited

U.S. PATENT DOCUMENTS

| | | | |
|---|---|---|---|
| 2,957,773 | 10/1960 | Toulmin, Jr. | 426/385 |
| 3,478,055 | 11/1969 | Shirakura et al. | 548/533 |
| 3,697,287 | 10/1972 | Winitz | 426/73 |
| 3,708,307 | 1/1973 | Lundstedt | 426/471 |
| 3,989,855 | 11/1976 | Jones et al. | 426/444 |
| 4,003,992 | 1/1977 | Beigler et al. | 424/101 |
| 4,141,783 | 2/1979 | Pisecky et al. | 426/471 |
| 4,219,589 | 8/1980 | Niks et al. | 427/213 |
| 4,229,249 | 10/1980 | Felsvang et al. | 159/4.01 |
| 4,279,917 | 7/1981 | Takami et al. | 514/400 |
| 4,579,747 | 4/1986 | Sugiyama et al. | 426/465 |
| 4,613,500 | 9/1986 | Suzuki et al. | 514/951 |

FOREIGN PATENT DOCUMENTS

| | | | |
|---|---|---|---|
| 34916 | 9/1981 | European Pat. Off. | |
| 54-55779 | 5/1979 | Japan | 426/471 |
| 886533 | 1/1962 | United Kingdom | 426/471 |
| 977908 | 12/1982 | U.S.S.R. | 426/465 |

OTHER PUBLICATIONS

Kirk-Othmer Ency. Chem. Tech., vol. 7, pp. 360–367, 1965 (USA).

*Primary Examiner*—Ronald W. Griffin
*Attorney, Agent, or Firm*—Jill H. Krafte

[57] ABSTRACT

A process is disclosed whereby a depyrogenated solution comprising one or more amino acids is converted to a dried, amorphous product by spray drying. The solution optionally may contain one or more additional components, such as salts, buffers, lipids, vitamins, trace elements and electrolytes. Products may be prepared according to this method which are suitable for enteral or parenteral nutritive therapeutic use.

23 Claims, No Drawings

PROCESS FOR SPRAY DRYING AMINO ACID COMPOSITIONS

BACKGROUND OF THE INVENTION

This invention relates generally to a simplified and effective process for the production of dried, high purity amino acids, which comprises depyrogenation and spray drying procedures. More specifically, chemically and physically homogeneous, rapidly dissolving products can be formulated which comprise one or more amino acids and which may further comprise salts, buffers, carbohydrates, lipids and/or micronutrients. The products formed by this process are particularly well suited for use in parenteral (intravenous) or enteral (oral or tube) nutritive supplement therapy.

Blends of amino acids find wide use as nutritive supplements. This type of nutritive therapy may be used for general nutritional enhancement, or may be designed to meet specific needs, such as the facilitation of post-operative wound healing or as an adjunct to the treatment of kidney disease, burns or trauma. For example, U.S. Pat. No. 3,697,287 (Winitz) discloses a composition palatable to humans which contains all of the essential amino acids, essential minerals and carbohydrate; U.S. Pat. No. 4,003,992 (Beigler et al.) and U.S. Pat. No. 4,279,917 (Takami et al.) disclose nutritionally acceptable amino acid solutions for intravenous administration. Parenteral and enteral nutritional supplements are subject to manufacturing standards and regulations of the Federal Drug Administration (FDA). Regulation of the manufacture of products for parenteral use is particularly stringent in terms of purity, sterility, formulation, etc. The regulations, which are strictly enforced, cover all aspects of processing, sampling, analysis and packaging. Products for enteral use must be produced by FDA-approved Good Manufacturing Practices (GMPs).

Conventional methods of formulating and packaging dried amino acids or blends thereof comprise the following series of process steps: Typically, an individual amino acid is dissolved in water, the solution is depyrogenated by ultrafiltration and the amino acid is crystallized from the solution. The crystals are removed by centrifugation, washed and dried to yield a single amino acid component. The dried, crystalline material may then be stored or physically blended with other amino acids, each prepared by the same series of steps. Each of these steps must be conducted in a sterile, or clean room, environment.

In addition to the costly and burdensome requirements for conducting these procedures in a sterile environment, significant quantities, i.e., 10 to 20%, of amino acids are lost by the use of conventional crystallization techniques. For example, somewhat less than 100%, i.e., about 85 to 95%, of the amino acid typically is recovered from the solution in crystalline form. Moreover, the solubility of the amino acid causes additional loss of product when the crystals are washed.

When intended for parenteral use, blends of crystalline amino acids generally are redissolved by a pharmaceutical company in water-for-injection, along with any other components, such as lipids or micronutrients, which are desired in the final preparation. The solution is loaded directly into intravenous bottles or the like, which are capped and terminally sterilized. Thus, it is bottles of sterile intravenous solutions which are shipped to and which must be stored by the hospitals, clinics and nursing homes which use them. Enteral products may be delivered in sterile packets for dissolution at the site of administration, or in sterile packets or containers of pre-dissolved product.

SUMMARY OF THE INVENTION

The method disclosed herein produces a dried amino acid or blend of amino acids which is particularly well suited for dissolution in a liquid carrier for use in parenteral or enteral nutritive therapy. Briefly, one or more amino acids are dissolved in a suitable solvent, passed through an ultrafiltration system for depyrogenation, spray dried as disclosed herein and collected into containers for shipping and/or storage. The dried product may be added to the liquid carrier at the point of use, since the product is capable of substantially instantaneous and uniform dissolution.

It is a primary objective of this invention to produce a dried amino acid composition which meets industry specifications for parenteral or enteral use and which possesses unique physical properties designed to enhance the usability of the composition. That is, the product of this invention should be chemically identical to conventionally prepared crystalline amino acids and should dissolve to form a solution which is chemically and physically indistinct from conventionally prepared amino acid solutions, and yet possess significant physical advantages in the dried form. For example, it is intended that the dried composition be capable of rapidly and completely dissolving in a suitable solvent under ambient conditions. Moreover, the dried product should be characterized by chemical and physical homogeneity, even after shipping and storage, so that it can be easily and quickly prepared for administration, while still ensuring that the solution actually used by the consumer is homogeneous.

An additional object is to enhance the economics of producing a dried amino acid product through improved recovery of the amino acid. Specifically, this method is intended to reduce loss of significant quantities of amino acid by eliminating the crystallization and washing steps of conventional methods. Moreover, it is an object of this invention to reduce the number of process steps required to be performed in a clean room environment.

It is further object to produce an amino acid product which can be shipped and stored in dried form until needed, thus reducing the costs attendant to shipping and storing the products.

DETAILED DESCRIPTION OF THE INVENTION

This invention presents a new process for preparing a dried, amorphous amino acid product. The process comprises the steps of dissolving at least one amino acid compound in a solvent, drying the resulting solution in a spray drier under conditions for producing a dried, amorphous product and collecting the dried product. In addition to the amino acid or acids, it is contemplated that one or more non-amino acid components or additives may be dissolved in the solvent. The amino acid component either is previously depyrogenated or is subjected to a depyrogenation process prior to the spray drying step.

The sources of the amino acid used in this invention may be varied. It is assumed, particularly for parenteral products, that the amino acids, and any other components intended for inclusion in the final product, are chemically pure and require only depyrogenation prior to the drying step. For enteral products, chemical purity may not be required, but the components must be of sufficient purity to meet product specifications. If the components are not suitably pure as purchased or formulated, conventional purification procedures are performed. These may include passage of the dissolved amino acid through activated carbon or charcoal beds for the removal of color bodies and/or passage through an ion exchange system for the removal of ionic compounds. If the former procedure is necessary or desirable, care should be taken to select carbon or charcoal which will not adsorb the amino acids as well, particularly if the solution comprises a specified blend of amino acids. The amino acids used in this invention should be of sufficient purity for the final dried product to meet the applicable industry specifications. Free amino acids may be used or the amino acids may be in the form of salts, such as acetic or hydrochloric acid salts, if desired.

It is contemplated that the process of this invention may be used to formulate single amino acid products or to formulate blended products. Any combination of two or more amino acids may be blended in the manner disclosed herein, and where the term "amino acid" is used, it may refer either to a single amino acid or to any combination of amino acids, unless otherwise specified.

It may be desired to include additional components in the final dried product, either with a single or multiple amino acids. For example, it is often desirable to administer to a patient salts, buffers, carbohydrates, lipids and/or micronutrients (which include vitamins, trace elements and electrolytes), together with amino acid therapy. It is possible to incorporate additional components, as long as they can be dissolved with the amino acids in the first step of this process, that is, if they are additives which are water soluble. It must be kept in mind, of course, that only additives approved for use in the final product, for example, in a parenteral solution, may be used. By including desired additives and multiple amino acids in the feed solution, specialty blends may be produced for particularized nutritional requirements. For enteral products intended for oral administration, it may be desired to include flavorings, nutritive sweeteners and/or non-nutritive sweeteners.

In the first step of this process, the selected amino acid (and other components, if desired) is dissolved in an aqueous solvent to form a feed solution. The procedures for weighing and adding the solution components are subject to control under standard FDA Good Manufacturing Practices. The choice of a suitable solvent will be guided by the end which is intended for the dried product. If the product will be used parenterally, the choice of solvents is limited by FDA regulation. For parenterals, the solvent typically will be USP standard water-for-injection. Other injectable liquids or FDA approved solvents meeting all FDA sterility and purity requirements may be used. For example, simple alcohols, such as ethanol, may be used, provided that if ethanol is the solvent, the process must be conducted under positive pressure nitrogen and in a closed cycle system. Aqueous ammonia may be used as long as care is taken to ensure that the dried product meets product specifications for residual ammonia. If the final product is intended for enteral use, the choice of solvents is, of course, wider. The initial components may be dissolved in water or other food-grade solvents or liquids. It is preferred that amino acid products intended for enteral use be prepared from sterile components, but the components and products at least should be processed and maintained under sanitary conditions.

The temperature and concentration of the amino acid may be varied. For the preparation of a single amino acid composition, it will be most economical to operate this process with the amino acid feed solutions at close to solubility limits, which, of course, will vary with the amino acid. Table I shows the solubilities of various amino acids in water from 25° to 75° C. It can be seen that the solubilities of individual crystalline amino acids are quite varied. If the dried product is to be a blend, the individual components of the feed solution are carefully controlled so that the feed solution will contain the amino acid and other components in the same relative concentrations as desired in the dried product. Alternatively, each component may be dissolved separaately to form separate stock solutions, and the stock solutions combined in such a manner that the desired blend is obtained. It is preferred that the blended feed solution be maintained at close to the solubility limit for the overall blend, again for reasons of economy.

TABLE I

| | (Solubilities of Amino Acids)[1] | | |
|---|---|---|---|
| Amino Acid | 20° C.[2] | 50° C.[2] | 75° C.[2] |
| L-Alanine | 16.70 | 23.00 | 31.90 |
| L-Arginine | 16.70 | 32.60 | 48.20[3] |
| L-Aspartic Acid | 0.50 | 1.20 | 2.80 |
| L-Cystine | 0.01 | 0.02 | 0.05 |
| L-Glutamic Acid | 0.84 | 2.19 | 5.53 |
| Glycine | 25.00 | 39.10 | 54.40 |
| L-Histidine | 4.29[4] | — | — |
| L-Isoleucine | 4.12 | 4.82 | 6.08 |
| L-Leucine | 2.33 | 2.66 | 3.82 |
| L-Phenylalanine | 2.97 | 4.43 | 6.62 |
| L-Proline | 162.00 | 207.00 | 239.00 |
| L-Serine | 5.02 | 10.30 | 19.20 |
| L-Tryptophan | 1.14 | 1.70 | 2.80 |
| L-Tyrosine | 0.05 | 0.11 | 0.24 |
| L-Valine | 8.80 | 9.60 | 10.24 |

[1]Data for Table I obtained from "Amino Acids & Related Compounds" (Kyowa Hakko) (2d Ed. 1978).
[2]Solubilities are in grams per 100 gm water.
[3]Solubility at 63° C.
[4]No temperature given for solubility figure.

The amino acid feed solution must be depyrogenated prior to drying, if not previously depyrogenated. The depyrogenation step is carried out in order to remove, to acceptable limits, pyrogens or endotoxins which may remain in the amino acid fermentation broth. These compounds usually are bacterial cell wall components released or left over after sterilization procedures. It is preferred to depyrogenate the feed solution immediately prior to spray drying, by ultrafiltration with a molecular weight cut-off of about 10,000 daltons. The molecular weight cutoff can be lower, if desired, but this will result in increased costs. Only after depyrogenation must the spray drying process of this invention be conducted in a clean room environment. Thus, only the drying and packaging steps will require sterile conditions. Alternatively, separate stock solutions prepared for each amino acid or other component may be individually depyrogenated before combining to form the feed solution. In that case, the sterility of the combined feed solution must be maintained from the time of its formation.

The feed solution may be maintained under air or an inert nitrogen atmosphere. It will, of course, be preferred as a matter of convenience to maintain the solution under air. However, if the temperature of the solution in the dissolution vessel is expected to approach about 85° to 90° C. or if the solution is to be held for an extended period, it may be desired to conduct the dissolution under nitrogen in order to avoid discoloration and the concomitant loss of light transmitting properties of the amino acid. The feed solution should be maintained under nitrogen until shortly before it is to be processed in the spray drier. For example, at about 85° C., discoloration can be expected within about 20 minutes when exposed to air, whereas the solution may be kept at that temperature under nitrogen for as long as 24 hours without discoloration.

The temperature of the solution in the dissolution vessel typically will be about 70° to 85° C. When water-for-injection ("WFI") is used as the solvent, the water will be at 80° C., pursuant to FDA regulations regarding operation of systems for producing WFI. Due to cooling upon leaving that system, the solution in the dissolution vessel will be about 6 to 8 degrees cooler, or about 72° to 74° C.

The depyrogenated feed solution is spray dried under suitable conditions to yield a homogeneous, free-flowing, white, amorphous product. Spray driers appropriate for use in this process operate by atomizing the feed solution to form a spray of droplets. The droplets are mixed with hot gases to evaporate the liquid, resulting in a dried product. Particularly for the preparation of parenterals, the drier is operated under positive pressure to reduce the potential for contamination. The gases and dried product are removed from the drier and separated, or are removed separately. For the preparation of parenterals, the drier should be cleaned and sterilized between each product batch. For the preparation of enteral products, cleaning and sterilization is preferred, but adequate cleaning to maintain sanitary conditions may be acceptable.

Several types of atomizing nozzles will be suitable for use with this process. A pressure nozzle or a two-fluid nozzle will be the most preferred. In the preparation of parenterals, it will be preferred not to use a mechanical atomizer, such as a spinning disk nozzle, since contamination may be introduced due to wearing of the nozzle parts or from lubrication of the disk. It may be possible to use this type of atomizer for enteral products, as long as product specifications can be met, but it is preferred to use non-mechanical atomizers in order to avoid contamination.

The pressure of the feed solution through the nozzle will depend on the nozzle design and the desired droplet size. A pressure nozzle may be run at a pressure of about 900 to about 1200 psig., preferably about 1000 to 1100 psig. A two fluid nozzle may be run at about 15 to about 30 psig. The preferred droplet size is about 40μ, but will vary with the nozzle type, drier type and drier temperature. These parameters, and the rate of feed of the depyrogenated amino acid solution through the nozzle, will be within the knowledge and ability of the process designer and must be specifically tailored for each situation.

The gas used in the spray drier may be any gas inert to the feed solution, but typically will be either air or nitrogen. For parenteral products, the gas must be sterile and uncontaminated. The gas preferably is filtered through a 0.22μ filter before entering the drier and may be sterilized by heat treatment. For enteral products, the sterility requirement will depend whether the end product itself must be sterile. As mentioned above, sterility is preferred, but in any case, sanitary conditions should be maintained.

The gas is heated to a desired temperature before being fed into the drier. The temperature of the gas inside the drier is critical in order to achieve the desired product: a white, amorphous amino acid composition meeting product specifications for moisture content. Typically, industrial specifications require the moisture content of dried amino acid products to be less than about three or four percent. The internal gas temperature most conveniently may be adjusted with reference to the gas outlet temperature, which is easily measured. By this method, the outlet temperature is maintained within the desired operational range by means of incremental adjustments to the gas inlet temperatures in order to make necessary corrections. In another embodiment, the temperature may be controlled by directly measuring and adjusting the inlet temperature and/or admixing a stream of colder gas as well.

The minimum outlet temperature should be about 95° to 100° C. Temperatures below this will tend to result in a wet, clumped product. The maximum outlet temperature should be about 135° to 150° C. Temperatures above this will cause "scorching" and discoloration of the product, and may also cause product decomposition and/or racemization. The most preferred gas outlet temperature range is about 100° to about 125° C. It has been found that there is little variability in the desired outlet temperature from one amino acid to another, or between blends and single amino acid products. The gas inlet pressure must be sufficient to maintain positive pressure inside the drier.

The residence time of the material in the drier is measured from the point of atomization by the nozzle to the point of outlet from the drying compartment. Residence time is regulated by gas flow and will be a function of drier design and size, temperature and the desired moisture content of the amino acid product. The typical water content of the spray dried material of this invention is about 2.0% but may range from about 1.0% to about 7.0%.

The dried product is separated from the drying gases, preferably within the drier itself, although not necessarily in the drying chamber. By internal separation, the product is protected from potential sources of contamination. It will be possible, however, to conduct the product and gas to a separate collection system, as long as appropriate precautions are taken to prevent product contamination. For example, the gas and dried material may be conducted aseptically to a cyclone separator. The precise means of separation will be within the knowledge and skill of the process designer.

The dried product may be packaged into any sterile container which is suitable for storage and shipment and which complies with FDA regulations. For parenteral products, the regulations require packaging materials and design adequate to maintain sterility of the packaged product for its anticipated shelf life. The dried parenteral product should be packaged directly from the drier or separator outlet, under sterile or clean room conditions. For enteral products, it is preferred that sterility be maintained, but requirements in this regard will depend on the product specifications. The dried amino acid product may be packaged in bulk containers for later re-packaging and distribution, or may be packaged individually for direct use. In this context, "individual" packaging means either pre-measured single portion packets or multiple-portion packets which are appropriate for consumer use. The latter may be especially useful for enteral products.

The final product preferably is sampled for analysis of composition, sterility, moisture content and total volatiles content. Conventional means of analysis may be utilized. Sampling, in accordance with a statistically designed sampling program, most conveniently may be done at the time of packaging directly following spray drying but it may be done at a later time, if desired.

The final product is a dried, amorphous composition whose physical and chemical homogeneity allows for substantially instantaneous dissolution in a liquid carrier for use as a nutritional supplement. The dissolution rate for an amino acid composition dried in the process of this invention is at least one order of magnitude faster than that for conventionally crystallized amino acids. Shaking or other agitation will aid dissolution. The time for dissolution will vary somewhat, depending on temperature, the solvent used and the desired concentration. Parenterals are dissolved in WFI to a concentration of about 5 to about 8.5%. The dissolution time for the spray dried composition is about 0.5 to 2.5 minutes, while the corresponding time for crystallized amino acids is about 5 to 25 minutes.

If the amino acid feed solution comprises several amino acids, or amino acid and one or more additives, the dried particles produced by this process each comprise a mixture of the solution components in the same proportions as those components were present in the feed solution. Pure particles of individual components are not obtained. Rather, the bulk product and each individual particle are homogeneous. Therefore, handling or shipping of the dried product does not result in the settling or separation of individual components of the blend. Moreover, as a dried blend prepared by the method of this invention is dissolved in a liquid carrier, the dissolution profile of the spray dried material is such that the composition of the solution (i.e., the distribution of dissolved amino acids) is substantially completely uniform over time, notwithstanding variation in the solubility rates for individual component amino acids. This stands in marked contrast with the dissolution of physical blends of crystalline amino acids, in which each amino acid dissolves according to its individual rate of dissolution.

An amino acid blend prepared by this process for parenteral use may be mixed with an appropriate quantity of WFI and administered intraveneously for nutritive supplementation. Because of the rapidity and uniformity of dissolution of this product, it may be dissolved in WFI at any time prior to administration, even at bedside. The solution then is administered intravenously for nutritive supplementation.

In another embodiment, a blend prepared for enteral use may be mixed with water or other liquid for oral or tube feeding. When employed as a nutritional supplement for oral consumption, the amino acid product may be mixed with any potable liquid such as juice, milk or the like, or any food containing sufficient moisture to dissolve the product. Other uses for amino acid products prepared by the method of this invention may include food additives or animal feed components.

The examples which follow are given for illustrative purposes and are not meant to limit the invention described herein. The following abbreviations have been used throughout in describing the invention:

| | |
|---|---|
| °C. | degree(s) Centigrade |
| °F. | degree(s) Fahrenheit |
| FDA | Food and Drug Administration |
| gm | gram(s) |
| GMP | Good Manufacturing Practice |
| HPLC | high pressure liquid chromotography |
| hr | hour(s) |
| M | molar |
| mg | milligram(s) |
| min | minutes |
| ml | milliliter(s) |
| μ | micron(s) |
| % | percent |
| psig | pounds per square inch gauge |
| USP | United States Pharmacopeia |
| WFI | water-for-injection |

EXAMPLE I

Single Amino Acid Products

Individual solutions of the amino acids and solvents listed in Table II were prepared at the indicated temperatures.

TABLE II (Amino Acid Solutions)

| Sample No. | Amino Acid (Lot No.)[1] | Solvent | Conc.[2] | Temp.[3] |
|---|---|---|---|---|
| 1 | Alanine (801230) | water[4] | 250.0 | 70 |
| 2 | Arginine (K33025) | water[4] | 667.0 | 70 |
| 3 | Cysteine HCl (10419) | water[4] | 1000.0 | 70 |
| 4 | Glycine (OCD) | water[4] | 500.0 | 70 |
| 5 | Histidine (195) | water[4] | 100.0 | 70 |
| 6 | Isoleucine (3-11-2) | water[4] | 55.0 | 70 |
| 7 | Leucine (2-3-3/1) | water[4] | 35.0 | 70 |
| 8 | Lysine HCl (820202) | water[4] | 1000.0 | 70 |
| 9 | Methionine (457) | water[4] | 90.0 | 70 |
| 10 | Phenylalanine (167) | ammonia[5] | 250.0 | 20 |
| 11 | Proline (K33199) | water[4] | 1333.0 | 70 |
| 12 | Serine (112) | water[4] | 779.8 | 70 |
| 13 | Threonine (TH37041) | water[4] | 180.0 | 70 |
| 14 | Tryptophan (THU34031) | ammonia[5] | 249.5 | 20 |
| 15 | Tyrosine (4-6-2) | ammonia[5] | 40.0 | 20 |
| 16 | Valine (301) | water[4] | 82.2 | 70 |

[1]Obtained from Welding GMBH, except for glycine (Organic Chemical Division of W. R. Grace & Co.).
[2]Concentration in grams per liter.
[3]Temperature in degrees Centigrade.
[4]Deionized water.
[5]14% aqueous ammonia (pH 12-13)

Four liters of each of the amino acid solutions listed in Table II were separately spray dried according to the following procedure: A Bowen Engineering Laboratory No. BE 499 spray drier was used, operated in a concurrent mode. Atomization was accomplished with an air driven two-fluid nozzle run at a pressure of 20.0 psig. The feed rate of the amino acid solution was 100 grams per minute. The spray drier was operated at an inlet hot air temperature of 210°–221° C.; the outlet temperature ranged from 106°–132° C. The residence time of the material in the drier ranged from 7.0 to 8.0 seconds. The drier was operated for the length of time necessary to process the entire sample, usually about 50 minutes for each sample.

The spray drier was examined between each sample of amino acid. No excessive buildup was observed other than a very light dusting normally found on operation of this type of spray drying equipment. Between each sample, the drier was cleaned with water.

The dried product formed from each of the above solutions was analyzed for amino acid content (by HPLC) and other components, i.e., degradation products (by HPLC and infra-red scans). Each spray dried product contained only the expected amino acid, with no degradation products or contaminants detected.

EXAMPLE II

Amino Acid Blend

A solution was prepared containing the amino acids listed in Table III. The solvent was de-ionized water, with the indicated amino acid quantities being grams per liter of water. The solution was formulated at 70° C.

The solution was spray dried according to the procedures described in Example I. The dried product was analyzed by dissolving, separating on a cation exchange liquid chromotography column and detecting amino acids by fluorescense as OPA (o-phthaldehyde) derivatives. The concentrations of the amino acid components in the dried blend were found to be approximately equal to those in the starting solution, as shown in Table III.

TABLE III (Multiple Component Amino Acid Solution)

| Amino Acid | Theoretical[1] | Measured[2] |
|---|---|---|
| Alanine | 7.28 | 7.92 |
| Arginine | 9.82 | 9.38 |
| Glycine | 14.40 | 14.10 |
| Histidine | 2.91 | 2.42 |
| Isoleucine | 7.13 | 6.99 |
| Leucine | 9.29 | 9.42 |
| Methionine | 5.42 | 5.04 |
| Proline | 11.50 | 13.20 |
| Threonine | 4.12 | 3.98 |
| Valine | 6.79 | 6.84 |

[1]Theoretical concentration (mg/ml).
[2]Measured concentration (mg/ml).

EXAMPLE III

Dissolution Rates

A 16 component blend of crystalline amino acids was obtained from Ajinomoto Co., Inc. for comparison with the spray dried amino acid material of this invention. The blend contained the amino acids indicated in Table IV. A 15 component spray dried amino acid product was selected as representative of the material prepared by the method of this invention. The component amino acids are indicated in Table IV.

TABLE IV

| Amino Acid | Blend[1] | Spray Dried[2] |
|---|---|---|
| Isoleucine | 4.67% | 7.09% |
| Leucine | 7.13% | 9.26% |
| Lycine-HCl | 8.36% | 9.97% |
| Methionine | 5.90% | 3.94% |
| Alanine | 12.29% | 12.60% |
| Arginine | 11.31% | 9.65% |
| Histidine | 2.70% | 2.95% |
| Proline | 14.75% | 8.47% |
| Phenylalanine | 8.46% | 4.33% |
| Threonine | 3.33% | 5.12% |
| Tryptophan | 1.72% | 1.58% |
| Valine | 5.51% | 7.88% |
| Serine | 2.95% | 4.14% |
| Glysine | 2.46% | 12.60% |
| Tyrosine | — | .43% |
| Glutamic Acid | 2.46% | — |
| Orthine-Aspartate | 2.46% | — |

[1]Crystalline blend from Ajinomoto Co., Inc. (expressed in weight percent).
[2]Spray dried material prepared according to invention. (expressed in weight percent).

For each test material, the solid sample was added to de-ionized water at room temperature (18° C.) with agitation (a stir bar). The intended final concentration of the solution was 8.5%, which is typical for commercial parenterals. Samples were removed from the beaker with a filtered syringe for measurement of percent amino acid in solution.

The blended material required 23 minutes to dissolve completely. At least 90% of the sample dissolved within 5 minutes and 38 seconds. The spray dried material dissolved completely within 2 minutes and 48 seconds and 97% of the sample was dissolved within 50 seconds. It was considered that the stir bar provided inadequate agitation and, therefore, the times were somewhat long for both materials.

EXAMPLE IV

Spray Drying of Commercial Preparation

A quantity of Travasol (TM) (Baxter Travenol Corp.) parenteral solution was spray dried according to the procedures of Example I. Table V indicates HPLC analysis data for the liquid and the spray dried material, was well as the analysis printed in the bottle label as purchased. It can be seen that spray drying the solution does not deleteriously effect the amino acid composition. In addition, the pH was 6.0 before and after spray drying, indicating that the buffering system (i.e., electrolytes) was unchanged by the spray drying process of this invention.

TABLE V

| Amino Acid | Label Analysis[1] | HPLC Liquid[1] | HPLC Spray Dried[1] |
|---|---|---|---|
| Alanine | 20.70 | 24.03 | 21.62 |
| Arginine | 10.35 | 10.54 | 11.95 |
| Glycine | 20.70 | 18.58 | 19.63 |
| Histidine | 4.38 | 3.16 | 4.24 |
| Isoleucine | 4.78 | 4.88 | 4.24 |
| Leucine | 6.19 | 6.43 | 5.24 |
| Lysine | 5.79 | 5.17 | 6.24 |
| Methionine | 5.79 | 5.63 | 5.24 |
| Phenylalanine | 6.19 | 6.27 | 6.73 |
| Proline | 4.19 | 4.49 | 4.99 |
| Threonine | 4.19 | 4.11 | 3.75 |
| Tyrosine | 0.40 | 0.34 | 0.25 |
| Tryptophan | 1.79 | 1.64 | 1.65 |
| Valine | 4.59 | 4.74 | 4.24 |

[1]data given in weight percent.

EXAMPLE V

Physical Stability

A solution containing 16 amino acids (threonine, serine, proline, glycine, alanine, valine, methionine, isoleucine, leucine, tyrosine, phenylalanine, lysine, histidine, arginine, tryptophan and cystine) was spray dried in a Niro Atomizer, Inc. S-28 drier, operated in a co-current mode. Atomization was accomplished with a pressure nozzle. The feed rate of the amino acid solution was 655 grams per minute, at a temperature of 70° C. The spray drier was operated at an inlet hot air temperature of 183° C.; the outlet temperature was 120° C. The product was about 40μ in diameter and had a total volatiles content of about 1.12–1.4%. The product density was 0.379 grams per cubic centimeter.

A five-gallon pail of the spray dried material was placed on a shaker for eight hours. Following shaking, samples of the material were taken from the top and bottom of the pail. Amino acid analysis of the two samples showed no significant differences, demonstrating that the spray dried material does not separate into its component amino acids as would a conventional physical blend.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing a dried, amorphous product comprising at least one amino acid, said process comprising:
   (a) dissolving at least one amino acid in a solvent,
   (b) driving the resulting solution in a spray drier by injecting the amino acid solution, at a temperature of about 70° to about 90° C., into said spray drier by means of an atomizing nozzle while introducing into said spray drier heated, sterile air or inert gas, while operating said spray drier such that the outlet temperature is about 95° to about 150° C., and
   (c) collecting the dried, amorphous product, said product characterized by (i) being physically and chemically homogeneous, (ii) having a moisture content of up to about 7 percent, (iii) dissolving substantially instantaneously in a liquid carrier, and (iv) having a dissolution profile such that the distribution of dissolved amino acid in solution is substantially completely uniform over time.

2. The process of claim 1 in which said amino acid is chemically pure.

3. The process of claim 1 in which said amino acid of step (a) has been depyrogenated.

4. The process of claim 1 in which the solution prepared as described in step (a), or a combination of two or more solutions prepared as described in step (a), is subjected to a depyrogenation process prior to step (b).

5. The process of claim 4 in which depyrogenation is by ultrafiltration.

6. The process of claim 1 in which two or more solutions prepared as described in step (a) are combined for processing as described in step (b).

7. The process of claim 1 in which the solution prepared as described in step (a), or a combination of two or more solutions prepared as described in step (a), is passed through an ion exchange system or a carbon bed or both prior to drying in step (b).

8. The process of claim 1 in which the solution prepared as described in step (a) also comprises at least one composition selected from the group consisting of salts, buffers, ligpids, vitamins, trace elements, electrolytes, flavorings and nutritive or non-nutritive sweeteners.

9. The process of claim 1 in which said solvent is suitable for use in the preparation of enteral or parenteral compositions.

10. The process of claim 9 in which said solvent is water, water for injection, aqueous ammonia or ethanol.

11. The process of claim 1 in which said atomizing nozzle is a pressure nozzle or a two-fluid nozzle.

12. The process of claim 1 in which said procedures further comprise operating said spray drier under positive pressure.

13. The process of claim 1 in which said outlet temperature is about 100° to 125° C.

14. The process of claim 1 in which at least 95 percent of the dissolved amino acid is recovered as dried product.

15. The process of claim 1 in which said dried product collected in step (c) is packaged in bulk or individual quantities.

16. The process of claim 1 which further comprises opeating in a closed system from the points of entry of the heated, sterile air or inert gas and entry of the amino acid solution to the point of collection of the dried product in sterile packaging or containers in step (c).

17. The process of claim 1 in which steps (b) and (c) are conducted in an environment designed to maintained the sterility and purity of the dried product.

18. The process of claim 17 in which said spray drier has means for distributing the dried product directly into sterile collection containers.

19. A process for preparing a dried composition comprising one or more amino acids and suitable for use in parenteral nutritive thereapy, comprising:
   (a) dissolving at least one chemically pure amino acid in a solvent meeting FDA requirements for use in preparation of products for parenteral use, spray drying the prepared solution under sterile conditions by injecting the resulting amino acid solution, at a temperature of about 70° to about 90° C., into a spray drier by means of an atomizing nozzle while introducing into said spray drier heated, sterile air or inert gas, while operating said spray drier such that the outlet temperature is about 95° to about 150° C., and
   (c) collecting the dried product under sterile conditions, said product characterized by (i) being physically and chemically homogeneous, (ii) having a moisture content of up to about 7 percent, (iii) dissolving substantially instantaneously in a liquid carrier, and (iv) having a dissolution profile such that the distribution of dissolved amino acid in solution is substantially completely uniform over time.

20. The process of claim 19 in which two or more solutions prepared as described in step (a) are combined.

21. The process of claim 19 in which the solution prepared in step (a) is subjected to a depyrogenation process.

22. The process of claim 19 in which the dried product collected in step (c) is pre-measured for individual parenteral dosages and packaged in sterile containers.

23. The process of claim 19 in which at least one composition selected from the group consisting of salts, buffers, lipids, vitamins, trace elements and electrolytes is dissolved in the amino acid solution of step (a).

* * * * *

UNITED STATES PATENT AND TRADEMARK OFFICE
CERTIFICATE OF CORRECTION

PATENT NO. : 4,734,401
DATED : March 29, 1988
INVENTOR(S) : John J. Blouin

It is certified that error appears in the above-identified patent and that said Letters Patent is hereby corrected as shown below:

Claim 1, line 5: "driving" should be --drying--.

Claim 8, line 4: "ligpids," should be --lipids,--.

Claim 17, lines 2-3: "maintained" should be --maintain--.

Claim 19, line 3: "thereapy," should be --therapy,--.

Signed and Sealed this

Twelfth Day of July, 1988

Attest:

DONALD J. QUIGG

Attesting Officer      Commissioner of Patents and Trademarks